United States Patent
Krarup (10) Patent No.: US 10,047,354 B2
(45) Date of Patent: Aug. 14, 2018

(54) REDUCTION OF DIMER CONTENT IN FACTOR VII POLYPEPTIDE COMPOSITIONS BY HEAT TREATMENT

(75) Inventor: Janus Krarup, Gentofte (DK)

(73) Assignee: Novo Nordisk Health Care AG, Zurich (CH)

( * ) Notice: Subject to any disclaimer, the term of this patent is extended or adjusted under 35 U.S.C. 154(b) by 178 days.

(21) Appl. No.: 12/675,004

(22) PCT Filed: Aug. 22, 2008

(86) PCT No.: PCT/EP2008/061011
§ 371 (c)(1),
(2), (4) Date: Mar. 18, 2010

(87) PCT Pub. No.: WO2009/027334
PCT Pub. Date: Mar. 5, 2009

(65) Prior Publication Data
US 2011/0003363 A1    Jan. 6, 2011

Related U.S. Application Data (60) Provisional application No. 60/969,785, filed on Sep. 4, 2007.

(30) Foreign Application Priority Data

Aug. 24, 2007  (EP) .................................. 07114950

(51) Int. Cl.
*A61K 38/00* (2006.01)
*C12N 9/64* (2006.01)

(52) U.S. Cl.
CPC .... *C12N 9/6437* (2013.01); *C12Y 304/21021* (2013.01)

(58) Field of Classification Search
None
See application file for complete search history.

(56) References Cited

U.S. PATENT DOCUMENTS

| | | | |
|---|---|---|---|
| 4,880,913 A | 11/1989 | Doleschel et al. | |
| 6,777,390 B1 * | 8/2004 | Matthiessen et al. | ....... 514/14.3 |
| 2007/0037966 A1 * | 2/2007 | Rasmussen et al. | .......... 530/383 |
| 2007/0049523 A1 | 3/2007 | Hansen et al. | |

FOREIGN PATENT DOCUMENTS

| | | |
|---|---|---|
| RU | 2357751 C2 | 6/2009 |
| WO | WO 01/77141 | 10/2001 |
| WO | 2005/117948 A1 | 12/2005 |
| WO | 2006/024497 A1 | 3/2006 |
| WO | 2006/114448 A2 | 11/2006 |
| WO | 2007/026020 A1 | 3/2007 |

OTHER PUBLICATIONS

Vlieg et al.(J. of Thrombosis & Haemostasis, vol. 1, pp. 516-522).*
Pedersen et al.. Thermal effects on an enzymatically latent conformation of coagulation factore VIIa, Eur. J. Biochem.1999,vol. 261, pp. 124-129.
Tomokiyo, K. et al., "Large-Scale Production and Properties of Human Plasma-Derived Activated Factor VII Concentrate", Vox Sanguinis, 2003, vol. 84, pp. 54-64.
Bolognesi et al "Chapter 3—Physicochemical Principles of Protein Aggregation", Progress in Molecular Biology and Translational Science, 2013, vol. 177, pp. 53-72.
Cromwell et al "Self-association of Therapeutic Proteins, Implications for Product Development"; taken from the textbook Misbehaving Proteins: (Mis) Folding, Aggregation, and Stability (2006) pp. 313-330.
Shire et al "Challenges in Development of High Protein Concentration Formulations" Journal of Pharmaceutical Sciences, 2004, vol. 93, Issue 6, pp. 1390-1402.

* cited by examiner

*Primary Examiner* — Hope Robinson
(74) *Attorney, Agent, or Firm* — Jianjie Hu (57) ABSTRACT

The present application relates to a method of reducing the content of dimers in Factor VII polypeptide composition by heat treatment.

6 Claims, 4 Drawing Sheets

REDUCTION OF DIMER CONTENT IN FACTOR VII POLYPEPTIDE COMPOSITIONS BY HEAT TREATMENT

CROSS-REFERENCE TO RELATED APPLICATIONS

This application is a 35 U.S.C. § 371 national stage application of International Patent Application PCT/EP2008/061011 (published as WO2009/027334 A1), filed Aug. 22, 2008, which claimed priority of European Patent Application 07114950.4, filed Aug. 24, 2007; this application further claims priority under 35 U.S.C. § 119 of U.S. Provisional Application 60/969,785, filed Sep. 4, 2007.

FIELD OF THE INVENTION

The present invention relates to a method for reducing the content of dimers in Factor VII polypeptide compositions, in particular compositions comprising Factor VII variants.

BACKGROUND OF THE INVENTION

Factor VII, which is involved in the clotting cascade, has proven to be a useful therapeutic agent to treat a variety of pathological conditions. Accordingly, there is an increasing need for formulations comprising activated factor VII polypeptides that are pharmaceutically acceptable and exhibit a uniform and predetermined clinical efficacy.

During the commercial manufacture of factor VII polypeptides, avoiding the formation of aggregates such as di- and oligomers of the polypeptide of interest is a challenge. Such product-related impurities are unwanted because of their potential antigenicity. Typically, extremes of pH and high temperatures are avoided in order to control the formation of aggregates/dimers during production.

WO 2007/026020 A1 concerns a method of purifying a composition comprising factor VII and factor VIIa polypeptides of production biproducts, whilst minimising the concurrent formation of factor VII or factor VIIa auto-degradation products.

Hence, in connection with the manufacture of factor VII polypeptides, there is a need for a production step by which the presence of dimers (including higher oligomers) of the factor VII polypeptide is reduced without any significant loss of yield. This will result in a safer and more stable drug substance and eventually a safer and more stable drug product.

BRIEF DESCRIPTION OF THE INVENTION

The present invention has solved the before-mentioned problem by applying a heat treating step in order to reduce the content of dimers (and higher oligomers).

Specifically, the present invention provides a method of reducing the content of dimers in a composition comprising a Factor VII polypeptide, said method comprising the steps of:

(a) if necessary, adjusting the pH of said composition to a value in the range of 4.5-10.0 (as determined at 5° C.);
(b) heating the composition to a temperature in the range of 20-50° C. for a period of at least 5 minutes; and
(c) subsequently cooling the composition to a temperature of at the most 10° C.

DETAILED DESCRIPTION OF THE INVENTION

As mentioned above, the present invention relates to a method of reducing the content of dimers in a composition comprising a factor VII polypeptide. The method is advantageously applied in the final stage of the overall process for the production of a factor VII polypeptide, in that further manipulation of the composition, including heating, pH changes, contacting with chromatographic materials, etc. many cause renewed formation of dimers.

The method comprises the following steps of which step (a) is non-mandatory:

(a) if necessary, adjusting the pH of said composition to a value in the range of 4.5-10.0 (as determined at 5° C.);
(b) heating the composition to a temperature in the range of 20-50° C. for a period of at least 5 minutes; and
(c) subsequently cooling the composition to a temperature of at the most 10° C.

Composition Comprising Factor VII Polypeptide

When used herein, the expression "composition" is intended to mean a liquid composition, preferably an aqueous liquid composition, i.e. a composition comprising less than 5% of non-aqueous solvents. The composition to be used in the method comprises the factor VII polypeptide as well as certain impurities in the form of dimers.

The term "dimer" is intended to include true dimers as well as higher oligomers and aggregates (e.g. trimers, tetramers, etc.) of any factor VII polypeptide. It has been observed that some factor VII polypeptide variants have an increased tendency to form dimers, compared to wild type factor VII. The increased dimer formation may be explained by the fact that factor VII polypeptide variants have different structures than wild type factor VII, and, consequently, different properties. An example of such a different property is the temperature at which they unfold, i.e. their melting point. When factor VII polypeptides unfold, their surface becomes more hydrophobic and they may therefore tend to interact with other unfolded, hydrophobic factor VII polypeptides, thereby forming dimers. For this reason, the invention may be considered particularly, though not exclusively, applicable to compositions of such factor VII polypeptide variants.

The method of the invention is particularly useful for compositions having a relatively high content of dimers, i.e., the content of dimers in the untreated composition (i.e. before step (b)) is at least 3%, such as at least 4%, such as at least 5%, such as at least 6%, such as at least 8%, or even at least 10%.

The term "factor VII polypeptide" is described in more detail further below. Based on the preliminary observations, it is believed that the present invention is particularly suited for non-native forms of factor VII, such as factor VII variants, because polypeptides within this group appear to have a higher tendency to form dimers. Thus in one embodiment, the factor VII polypeptide used in the method according to the present invention is a non-wild type human factor VIIa, e.g. a Factor VII variant.

The factor VIIa concentration in the composition is conveniently expressed as mg/mL or as IU/mL, with 1 mg usually representing 43,000-56,000 IU or more. The concentration of the factor VII polypeptide in the composition is typically at least 0.01 mg/mL, or at least 0.1 mg/mL. In different embodiments, the factor VII polypeptide is present in the composition in a concentration of 0.1-90 mg/mL; 0.5-80 mg/mL; 1.0-80 mg/mL; 1.5-70 mg/mL; 2-60 mg/mL; 3-50 mg/mL; or 5-50 mg/mL.

The composition may before step (a), and in particular subsequent to any application of step (a), include a buffering agent (to be understood as a single agent or a combination of agents) which is capable of keeping the pH within the specified range, i.e. within 4.5-10.0.

In one embodiment, the buffering agent is at least one component selected from the groups consisting of acids and salts of MES, PIPES, ACES, BES, TES, HEPES, TRIS, histidine, imidazole, glycine, glycylglycine, glycinamide, phosphoric acid, acetic acid (e.g. sodium or calcium acetate), lactic acid, glutaric acid, citric acid, tartaric acid, malic acid, maleic acid, and succinic acid. It should be understood that the buffering agent may comprise a mixture of two or more components, wherein the mixture is able to provide a pH value in the specified range. As examples can be mentioned acetic acid and sodium acetate, etc.

The concentration of the buffering agent is chosen so as to maintain the preferred pH of the composition. In various embodiments, the concentration of the buffering agent is 1-100 mM; 1-50 mM; 1-25 mM; or 2-20 mM.

It has been observed that factor VII polypeptides are prone to autoactivation and—degradation as the pH is raised. On the other hand, factor VII polypeptides are more likely to dimerise and aggregate as the pH is decreased. The pH range of a factor VII polypeptide composition is selected such that the best compromise may be found between solving these two pH-related problems. Such pH ranges may be expected to differ between different factor VII polypeptides, whose chemical and therefore structural characteristics differ from the one to the other. In one embodiment of the invention, the pH of the composition is kept in the range of 4.5-10, such as in the range of 5-10; such as in the range of 9-10. In another embodiment of the invention, the pH of the composition is kept in the range of 4.5-9.5; such as in the range of 4.5-8.5; such as in the range of 4.5-7.5; such as in the range of 4.5-6.5; such as in the range of 4.5-6.0; such as in the range of 5.0-6.5; such as in the range of 5.0-6.0; such as in the range of 5.2 to about 5.9.

When reference is made to pH values, the value when measured at approximately 5° C. is applicable.

The composition is preferably kept at a temperature of at the most 10° C., in particular at the most 5° C., before application of the heat treatment (step (b)).

In a preferred embodiment, the composition comprises a calcium or magnesium salt, such as calcium chloride or calcium acetate. Calcium ions bind to the factor VII polypeptide and are necessary for the correct folding of the Gla domain of the factor VII polypeptide, such that the factor VII polypeptide, in particular its Gla domain, is protected from auto-proteolytic degradation. It is expected that magnesium ions could protect factor VII polypeptides in the same manner as calcium ions.

The composition may also include further constituents, e.g. tonicity modifying agents which contribute to the osmolality of the solution. Such tonicity modifying agent typically includes at least one agent selected from the group consisting of neutral salts, amino acids, peptides of 2-5 amino acid residues, monosaccharides, disaccharides, polysaccharides, and sugar alcohols. In some preferred embodiments, the composition comprises two or more of such agents in combination. By "neutral salt" is meant a salt that is neither an acid nor a base when dissolved in an aqueous solution.

In one embodiment, at least one tonicity modifying agent is a neutral salt selected from the groups consisting of sodium salts, potassium salts, calcium salts, and magnesium salts, such as sodium chloride, potassium chloride, calcium chloride, calcium acetate, calcium gluconate, calcium laevulate, magnesium chloride, magnesium acetate, magnesium gluconate, and magnesium laevulate.

In one preferred embodiment, the tonicity modifying agent includes sodium chloride in combination with at least one selected from the groups consisting of calcium chloride, calcium acetate, magnesium chloride and magnesium acetate.

In another preferred embodiment, the tonicity modifying agent is at least one selected from the group consisting of sodium chloride, calcium chloride, sucrose, glucose, and mannitol.

Typically, the tonicity modifying agent is present in a concentration of at least 1 mM, at least 5 mM, at least 10 mM, at least 20 mM, at least 50 mM, at least 100 mM, at least 200 mM, at least 400 mM, at least 800 mM, at least 1000 mM, at least 1200 mM, at least 1500 mM, at least 1800 mM, at least 2000 mM, or at least 2200 mM.

In one series of embodiments, the tonicity modifying agent is present in a concentration of 5-2200 mM, such as 25-2200 mM, 50-2200 mM, 100-2200 mM, 200-2200 mM, 400-2200 mM, 600-2200 mM, 800-2200 mM, 1000-2200 mM, 1200-2200 mM, 1400-2200 mM, 1600-2200 mM, 1800-2200 mM, or 2000-2200 mM; 5-1800 mM, 25-1800 mM, 50-1800 mM, 100-1800 mM, 200-1800 mM, 400-1800 mM, 600-1800 mM, 800-1800 mM, 1000-1800 mM, 1200-1800 mM, 1400-1800 mM, 1600-1800 mM; 5-1500 mM, 25-1400 mM, 50-1500 mM, 100-1500 mM, 200-1500 mM, 400-1500 mM, 600-1500 mM, 800-1500 mM, 1000-1500 mM, 1200-1500 mM; 5-1200 mM, 25-1200 mM, 50-1200 mM, 100-1200 mM, 200-1200 mM, 400-1200 mM, 600-1200 mM, or 800-1200 mM.

Often, the composition comprising the factor VII polypeptide is obtained from a preceding purification step. In a particularly relevant embodiment, an anion exchange chromatography step precedes step (a). It has been observed that a high concentration of factor VII polypeptide dimers is produced during this anion exchange step. Therefore, it is particularly useful to place this step before the adjustment of pH, heating and cooling steps of the present invention which together reduce the number of remaining dimers.

Factor VII Polypeptide

As used herein, the terms "factor VII polypeptide" or "FVII polypeptide" means any protein comprising the amino acid sequence 1-406 of wild-type human factor VIIa (i.e., a polypeptide having the amino acid sequence disclosed in U.S. Pat. No. 4,784,950), variants thereof as well as factor VII-related polypeptides, factor VII derivatives and factor VII conjugates. This includes factor VII variants, factor VII derivatives and factor VII conjugates exhibiting substantially the same or improved biological activity relative to wild-type human factor VIIa.

The term "factor VII" is intended to encompass factor VII polypeptides in their uncleaved (zymogen) form, as well as those that have been proteolytically processed to yield their respective bioactive forms, which may be designated factor VIIa. Typically, factor VII is cleaved between residues 152 and 153 to yield factor VIIa, i.e. the activated form of factor VII. Such variants of factor VII may exhibit different properties relative to human factor VII, including stability, phospholipid binding, altered specific activity, and the like.

"Factor VII" or "factor VIIa" within the above definition also includes natural allelic variations that may exist and occur from one individual to another. Also, degree and location of glycosylation or other post-translation modifications may vary depending on the chosen host cells and the nature of the host cellular environment.

As used herein, "wild type human FVIIa" is a polypeptide having the amino acid sequence disclosed in U.S. Pat. No. 4,784,950.

As used herein, "factor VII-related polypeptides" encompasses polypeptides, including variants, in which the factor VIIa biological activity has been substantially modified, such as reduced, relative to the activity of wild-type factor VIIa. These polypeptides include, without limitation, factor VII or factor VIIa into which specific amino acid sequence alterations have been introduced that modify or disrupt the bioactivity of the polypeptide.

The term "factor VII derivative" as used herein, is intended to designate a FVII polypeptide exhibiting substantially the same or improved biological activity relative to wild-type factor VII, in which one or more of the amino acids of the parent peptide have been genetically and/or chemically and/or enzymatically modified, e.g. by alkylation, glycosylation, PEGylation, acylation, ester formation or amide formation or the like. This includes but is not limited to PEGylated human factor VIIa, cysteine-PEGylated human factor VIIa and variants thereof. Non-limiting examples of factor VII derivatives includes GlycoPegylated FVII derivatives as disclosed in WO 03/31464 and US Patent applications US 20040043446, US 20040063911, US 20040142856, US 20040137557, US 20040132640, WO2007022512, and US 20070105755 (Neose Technologies, Inc.); FVII conjugates as disclosed in WO 01/04287, US patent application 20030165996, WO 01/58935, WO 03/93465 (Maxygen ApS) and WO 02/02764, US patent application 20030211094 (University of Minnesota).

The term "improved biological activity" refers to FVII polypeptides with i) substantially the same or increased proteolytic activity compared to recombinant wild type human factor VIIa or ii) to FVII polypeptides with substantially the same or increased TF binding activity compared to recombinant wild type human factor VIIa or iii) to FVII polypeptides with substantially the same or increased half life in blood plasma compared to recombinant wild type human factor VIIa.

The term "PEGylated human factor VIIa" means human factor VIIa, having a PEG molecule conjugated to a human factor VIIa polypeptide. It is to be understood, that the PEG molecule may be attached to any part of the factor VIIa polypeptide including any amino acid residue or carbohydrate moiety of the factor VIIa polypeptide.

The term "cysteine-PEGylated human factor VIIa" means factor VIIa having a PEG molecule conjugated to a sulfhydryl group of a cysteine introduced in human factor VIIa.

The term "factor VII variant" as used herein, is intended to designate a FVII polypeptide exhibiting substantially the same or better bioactivity than wild-type factor VII, or, alternatively, exhibiting substantially modified or reduced bioactivity relative to wild-type factor VII, and are polypeptides having an amino acid sequence that differs from the sequence of wild-type factor VII by insertion, deletion, or substitution of one or more amino acids.

Non-limiting examples of Factor VII variants having substantially the same or increased proteolytic activity compared to recombinant wild type human factor VIIa include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; factor VIIa that has been proteolytically cleaved between residues 290 and 291 or between residues 315 and 316 (Mollerup et al., Biotechnol. Bioeng. 48:501-505, 1995); oxidized forms of factor VIIa (Kornfelt et al., Arch. Biochem. Biophys. 363:43-54, 1999); FVII variants as disclosed in PCT/DK02/00189 (corresponding to WO 02/077218); and FVII variants exhibiting increased proteolytic stability as disclosed in WO 02/38162 (Scripps Research Institute); FVII variants having a modified Gla-domain and exhibiting an enhanced membrane binding as disclosed in WO 99/20767, U.S. Pat. No. 6,017,882 and U.S. Pat. No. 6,747,003, US patent application 20030100506 (University of Minnesota) and WO 00/66753, US patent applications US 20010018414, US 2004220106, and US 200131005, U.S. Pat. No. 6,762,286 and U.S. Pat. No. 6,693,075 (University of Minnesota); and FVII variants as disclosed in WO 01/58935, U.S. Pat. No. 6,806,063, US patent application 20030096338 (Maxygen ApS), WO 03/93465 (Maxygen ApS), WO 04/029091 (Maxygen ApS), WO 04/083361 (Maxygen ApS), and WO 04/111242 (Maxygen ApS), as well as in WO 04/108763 (Canadian Blood Services).

Non-limiting examples of FVII variants having increased biological activity compared to wild-type FVIIa include FVII variants as disclosed in WO 01/83725, WO 02/22776, WO 02/077218, WO 03/027147, WO 04/029090, WO 05/075635, and European patent application with application number 05108713.8 (Novo Nordisk A/S), WO 02/38162 (Scripps Research Institute); and FVIIa variants with enhanced activity as disclosed in JP 2001061479 (Chemo-Sero-Therapeutic Res Inst.).

Examples of variants of factor VII include, without limitation, P10Q-FVII, K32E-FVII, P10Q/K32E-FVII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V/M298Q-FVII, M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, 5314E/K316H-FVII, S314E/L305V-FVII, 5314E/K337A-FVII, 5314E/V158D-FVII, 5314E/E296V-FVII, 5314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/V158D/E296V/M298Q/S314E-FVII, F374Y/L305V/E296V/M298Q/V158T/S314E-FVII, F374Y/L305V/E296V/M298Q/K337A/V158T-FVII, F374Y/L305V/E296V/K337A/V158T/S314E-FVII, F374Y/L305V/M298Q/K337A/V158T/S314E-FVII, F374Y/L305V/V158D/E296V/M298Q/K337A-FVII, F374Y/L305V/V158D/E296V/K337A/S314E-FVII, F374Y/L305V/V158D/M298Q/K337A/S314E-FVII, F374Y/L305V/E296V/M298Q/K337A/V158T/S314E-FVII, F374Y/L305V/V158D/E296V/M298Q/K337A/S314E-FVII, S52A-Factor VII, S60A-Factor VII; R152E-Factor VII, S344A-Factor VII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn; FVII having substitutions, additions or deletions in the amino acid sequence from 304Arg to 329Cys; and FVII having substitutions, additions or deletions in the amino acid sequence from 153Ile to 223Arg.

Thus, substitution variants in a factor VII polypeptide include, without limitation substitutions in positions P10, K32, L305, M306, D309, V158, E296, K337, M298, S336, S314, K316, F374, S52, S60, R152, S344, T106, K143, N145, V253, R290, A292, G291, R315, V317, and substitutions, additions or deletions in the amino acid sequence from T233 to N240 or from R304 to C329; or from I153 to R223, or combinations thereof, in particular variants such as P10Q, K32E, L305V, M306D, D309S, L305I, L305T, F374P, V158T, M298Q, V158D, E296V, K337A, M298Q, M298K, S336G, S314E, K316H, K316Q, F374Y, S52A, S60A, R152E, S344A, T106N, K143N, N145T, V253N, R290N, A292T, G291N, R315N, V317T, and substitutions, additions or deletions in the amino acid sequence from T233 to N240, or from R304 to C329, or from I153 to R223, or combinations thereof.

The biological activity of factor VIIa in blood clotting derives from its ability to (i) bind to Tissue Factor (TF) and (ii) catalyze the proteolytic cleavage of factor IX or factor X to produce activated factor IX or X (factor IXa or Xa, respectively).

For the purposes of the invention, biological activity of factor VII polypeptides may be quantified by measuring the ability of a preparation to promote blood clotting, cf. Assay 4 described herein. In this assay, biological activity is expressed as the reduction in clotting time relative to a control sample and is converted to "factor VII units" by comparison with a pooled human serum standard containing 1 unit/mL factor VII activity. Alternatively, factor VIIa biological activity may be quantified by (i) measuring the ability of factor VIIa or a factor VII-related polypeptide to produce activated factor X (Factor Xa) in a system comprising TF embedded in a lipid membrane and factor X. (Persson et al., J. Biol. Chem. 272:19919-19924, 1997); (ii) measuring factor X hydrolysis in an aqueous system ("In Vitro Proteolysis Assay", see Assay 2 below); (iii) measuring the physical binding of factor VIIa or a factor VII-related polypeptide to TF using an instrument based on surface plasmon resonance (Persson, FEBS Letts. 413:359-363, 1997); (iv) measuring hydrolysis of a synthetic substrate by factor VIIa and/or a factor VII-related polypeptide ("In Vitro Hydrolysis Assay", see Assay 1 below); or (v) measuring generation of thrombin in a TF-independent in vitro system (see Assay 3 below).

Factor VII variants having substantially the same or improved biological activity relative to wild-type factor VIIa encompass those that exhibit at least about 25%, preferably at least about 50%, more preferably at least about 75% and most preferably at least about 90% of the specific activity of factor VIIa that has been produced in the same cell type, when tested in one or more of a clotting assay (Assay 4), proteolysis assay (Assay 2), or TF binding assay as described above. Factor VII variants having substantially reduced biological activity relative to wild-type factor VIIa are those that exhibit less than about 25%, preferably less than about 10%, more preferably less than about 5% and most preferably less than about 1% of the specific activity of wild-type factor VIIa that has been produced in the same cell type when tested in one or more of a clotting assay (Assay 4), proteolysis assay (Assay 2), or TF binding assay as described above. Factor VII variants having a substantially modified biological activity relative to wild-type factor VII include, without limitation, factor VII variants that exhibit TF-independent factor X proteolytic activity and those that bind TF but do not cleave factor X.

Step (a)—Adjustment of pH

In the first non-mandatory step (a), the pH of the composition is, if necessary, adjusted to a value in the range of 4.5-10.0. As mentioned above, this is typically achieved by addition of one or more buffering agents. Compositions already having a pH within the specified range need—of course—not to be adjusted with respect to pH, but it may be desirable to adjust the pH, e.g. in view of any subsequent activation and formulation steps.

The step of adjusting the pH of the composition may also include dilution or concentration (e.g. evaporation of solvent) of the composition.

The composition is preferably kept at a temperature of at the most 10° C., in particular at the most 5° C., more particular close to 0° C., during step (a).

Step (b)—Heat Treatment

Heat treatment is the crucial step of the method of reducing the content of dimers in the composition.

It has been found that the heating temperature should be at least 20° C. in order for the reduction of the dimer content to take place, at least within a reasonable time frame, e.g. within 72 hours. On the other hand, it is believed that a heating temperature of more than 50° C. will cause the risk of denaturation (and thereby deactivation) of the Factor VII polypeptide.

Heating to the desired temperature can be achieved by placing a container containing the composition in a thermostated bath, for example, an oil bath or a water bath, or in an oven. The period of time required to reach the desired temperature will i.a. depend on the heat transmission coefficient of the container vs. the surrounding medium. It is often desirable, that the desired temperature is reached as fast as possible, or at least that a temperature of 20° C., or a temperature approximately 5° C. below the set-point, is reached as fast as possible.

In alternative embodiments, the heat treatment is conducted in batch or continuous mode in a flow-through reactor, where the flow-through time corresponds to the desired period of time for the heat treatment. A number of practical embodiments will be apparent for the person skilled in the art.

The desirable temperature and the necessary period of time for the heat treatment can, e.g., be determined in a model example as the one described as Example 2 herein. The minimum required period of time for the heat treatment is typically about 5 minutes, such as 10 minutes, whereas the maximum period of time in principle may be several or many days, eg. 168 hours. For practical reasons, the period of time for the treatment is preferable from 10 minutes to 72 hours.

It is believed that prolonged heat treatment might cause the formation of dimers of a type different from the type which is reduced by the heat treatment. This hypothesis is supported by observations in Example 2, wherein heat treatment at 37° C. for more than 10 hours actually results in a significant (re-)formation of dimers.

This being said, the preferred period of time for the heat treatment at 30-45° C. is typically 10-600 minutes. The preferred period of time for the heat treatment at 20-30° C. is typically 5-72 hours, and the preferred period of time for the heat treatment at 35-50° C. is typically 10-300 minutes. In the currently most preferred embodiment, the heat treatment takes place at around 37° C. for 10-120 minutes.

It should be understood that optimisation of the method of the invention might lead to a heat treatment not necessarily involving a constant temperature, but that it might turn out to be advantageous to utilize a gradual or step-wise increase of the temperature and/or a gradual step-wise reduction of the temperature within the overall temperature range of 20-50° C.

The purpose of the heat treatment is to reduce the content of dimers in the composition comprising the factor VII polypeptide. In particular, a significant reduction should be expected in order to justify the additional steps in the over-all production process. Therefore, it is preferred that the level of dimers (as determined by the HMWP GPC method described herein) in said composition expressed as %-points relative to the total pool of factor VII polypeptide has been reduced by at least a factor of 1.2, such as by at least a factor of 1.5, in particular at least a factor of 2, or even at least a factor of 3.

It is envisaged that the content of dimers can be reduced to a level of below 5%, in particular to a level below 4%, and more preferable to a level below 3%, or even to a level below 2% or even more preferred to a level below 1.5%.

Step (c)—Cooling

The composition is subsequently cooled to a temperature of at the most 10° C., e.g. at the most 5° C. It is advantageous to conduct the cooling fairly rapidly, e.g. by cooling in an ice bath (approx. 0° C.), or by adding ice to the composition. Alternatively, and as above, the cooling may be conducted in a flow-through reactor. By rapid cooling, prolonged existence of conditions at which dimers may be re-formed (e.g. at temperatures of 5-15° C.) can be avoided.

After cooling, the composition may undergo further process steps. It is taken into account that such process steps should preferably not cause any significant re-formation of dimers. This being said, in a preferred embodiment, the factor VII polypeptide is activated in a step subsequent to step (b), i.e. the factor VII polypeptide is activated either before or after cooling of the composition. Preferably, the factor VII polypeptide is activated in a step subsequent to the heating process because activation can be difficult to control during heating.

Preferred Embodiment

In one particularly preferred embodiment, the invention relates to a method of reducing the content of dimers in a composition comprising a factor VII variant, said method comprising the steps of:

(a) if necessary, adjusting the pH of said composition to a value in the range of 5.0-6.5;
(b) heating the composition to a temperature in the range of 30-45° C. for a period in the range of 20-600 minutes; and
(c) subsequently cooling the composition to a temperature of at the most 5° C.

Preferred Embodiment

In a second particularly preferred embodiment, the invention relates to a method of reducing the content of dimers in a composition comprising a factor VII variant, said method comprising the steps of:

(a) if necessary, adjusting the pH of said composition to a value in the range of 9.0-10.0;
(b) heating the composition to a temperature in the range of 30-45° C. for a period in the range of 20-600 minutes; and
(c) subsequently cooling the composition to a temperature of at the most 5° C.

Preparation and Purification of Factor VII Polypeptides

Human purified factor VIIa applicable in the method of the present invention is preferably made by DNA recombinant technology, e.g. as described by Hagen et al., Proc. Natl. Acad. Sci. USA 83: 2412-2416, 1986, or as described in European Patent No. 0 200 421 (ZymoGenetics, Inc.).

Factor VII may also be produced by the methods described by Broze and Majerus, J. Biol. Chem. 255 (4): 1242-1247, 1980 and Hedner and Kisiel, J. Clin. Invest. 71: 1836-1841, 1983. These methods yield factor VII without detectable amounts of other blood coagulation factors. An even further purified factor VII preparation may be obtained by including an additional gel filtration as the final purification step. Factor VII is then converted into activated factor VIIa by known means, e.g. by several different plasma proteins, such as factor XIIa, IXa or Xa. Alternatively, as described by Bjoern et al. (Research Disclosure, 269 September 1986, pp. 564-565), factor VII may be activated by passing it through an ion-exchange chromatography column, such as Mono Q® (Pharmacia fine Chemicals) or the like, or by autoactivation in solution. The method steps of the invention are preferably applied immediately before the activation of the factor VII polypeptide.

Factor VII-related polypeptides may be produced by modification of wild-type factor VII or by recombinant technology. Factor VII-related polypeptides with altered amino acid sequence when compared to wild-type factor VII may be produced by modifying the nucleic acid sequence encoding wild-type factor VII either by altering the amino acid codons or by removal of some of the amino acid codons in the nucleic acid encoding the natural factor VII by known means, e.g. by site-specific mutagenesis.

It will be apparent to those skilled in the art that substitutions can be made outside the regions critical to the function of the factor VIIa molecule and still result in an active polypeptide. Amino acid residues essential to the activity of the factor VII polypeptide, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for coagulant, respectively cross-linking activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The introduction of a mutation into the nucleic acid sequence to exchange one nucleotide for another nucleotide may be accomplished by site-directed mutagenesis using any of the methods known in the art. Particularly useful is the procedure that utilizes a super-coiled, double-stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemi-methylated DNA to digest the parental DNA template and to select for mutation-containing synthesized DNA. Other procedures known in the art for creating, identifying and isolating variants may also be used, such as, for example, gene shuffling or phage display techniques.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, factor VII polypeptides may be further purified. Purification may be achieved using any method known in the art, including, without limitation, affinity chromatography, such as, e.g., on an anti-factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J. C. Janson and Lars Ryden, editors, VCH Publishers, New York, 1989. Following purification, the preparation preferably contains less than 10% by weight, more preferably less than 5% and most preferably less than 1%, of non-Factor VII polypeptides derived from the host cell.

Factor VII polypeptides may be activated by proteolytic cleavage, using factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, factor VII polypeptides may be activated by passing it through an ion-exchange chromatography column, such as Mono Q® (Pharmacia) or the like, or by autoactivation in solution. The method steps of the invention are—as mentioned above—preferably applied immediately before the activation of the factor VII polypeptide.

The resulting activated factor VII polypeptide may then be formulated and administered as described in the art.

The following examples illustrate practice of the invention. These examples are included for illustrative purposes only and are not intended in any way to limit the scope of the invention claimed.

EXAMPLES

Methods
Determination of Dimer Content—HMWP GPC Method

SE-HPLC, a size exclusion chromatography method, was used to analyse FVIIa samples under nondissociating conditions. The content of HMWP (high molecular weight proteins), i.e. FVIIa aggregates in the form of dimers, oligomers and polymers, was determined by area % relative to the monomer target product peak.

The column used was a Waters Protein Pak 300 SW (7.5*300 mm, corresponding to a column volume of 13.25 mL) or a column with similar specifications. General analytical conditions were:

Temperature: RT (21-25° C.); detection: UV-detection at the column outlet at 215 nm; flow: 0.5 ml/min corresponding to 2.25 CV/hr.

The analytical run was performed using a running buffer with the following composition: 0.2 M ammonium sulphate, 5% isopropanol, adjusted to pH 7.0.

Following column equilibration and using 0.5 CV of running buffer, FVIIa samples containing approximately 1 mg FVIIa/ml were thawed and analysed concentrated by injecting a sample volume of 25 microliters (corresponding to a sample volume of 0.2% relative to the column volume). The sample was followed by elution for 1.5 CV.

Figure 3:
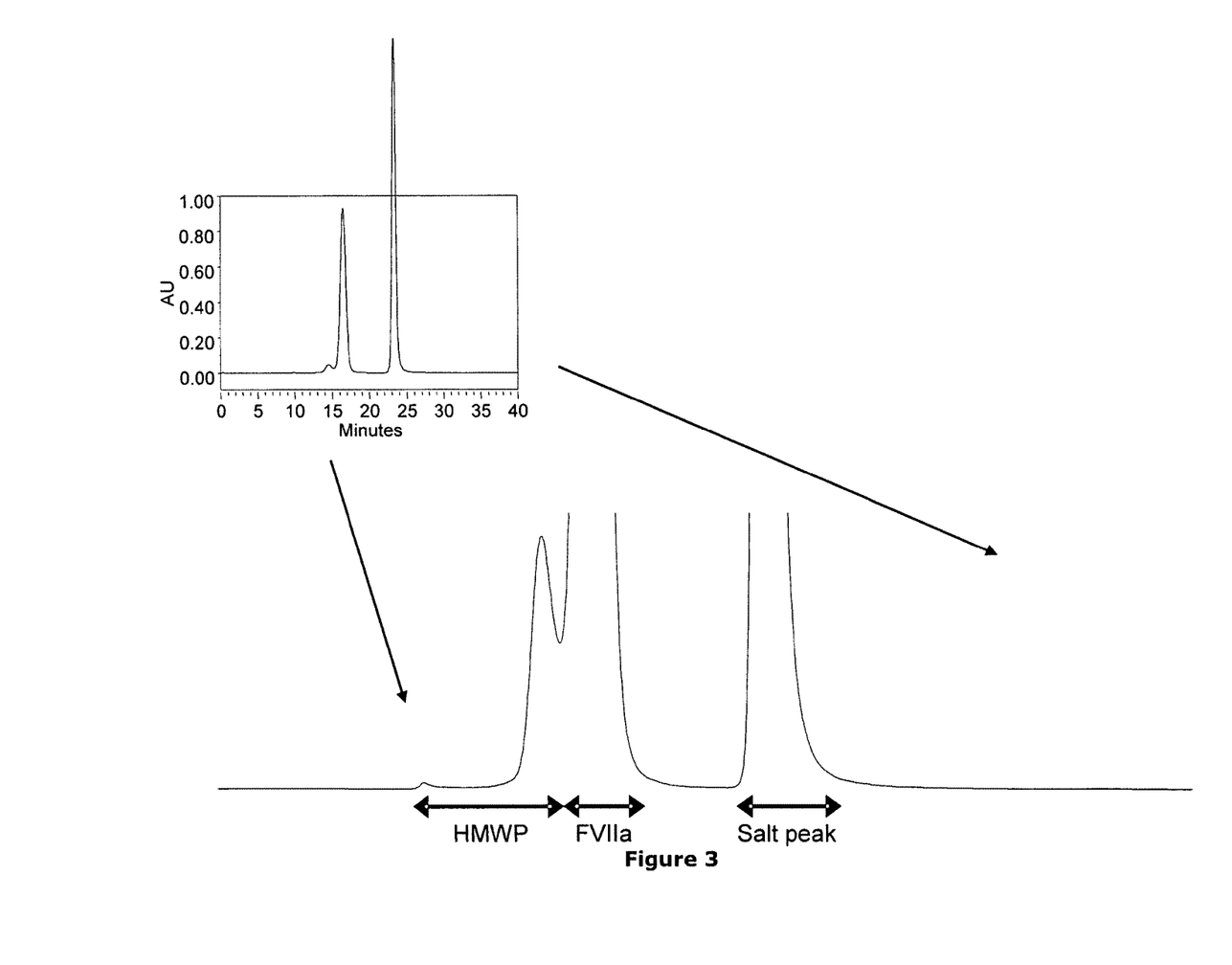
FIG. 3 illustrates the amount of HMWP (polymer and oligomer), monomer and salt that remains after the completion of the invention described herein.

A chromatogram typically consists of two major peaks and two minor peaks, as illustrated in FIG. 3. As viewed from the left, two minor peaks are observed which represent HMWP (polymer and dimer/oligomer peaks). The first major peak represents the monomer of FVIIa and the second major peak represents the salt peak.

Example 1—Heat Treatment of Factor VIIa Variant at 37° C.

A 1.5 mg/mL solution of a FVIIa variant in 15 mM $CaCl_2$, 30 mM NaCl, 10 mM Histidine, pH 6.0 (at 5° C.) was filtered through a 0.22 micron filter into a 700 mL HDPE bottle. pH was adjusted to 5.8 (at 5° C.) using 1M HCl or 1M NaOH. The bottle was placed in a water bath with a temperature of 37° C. Raising the temperature of the HDPE bottle to 37° C. took approximately 20 minutes. After 45 minutes of the solution having reached 37° C., the reaction was stopped by placing the bottle on ice.

The initial dimer content was determined to 7.3% by GPC and was reduced to 2.8% following the heat treatment. Hence heat treatment at 37° C. for 45 minutes appears to be sufficient in order to reduce the dimer content by a factor of more than 2.

Figure 1:
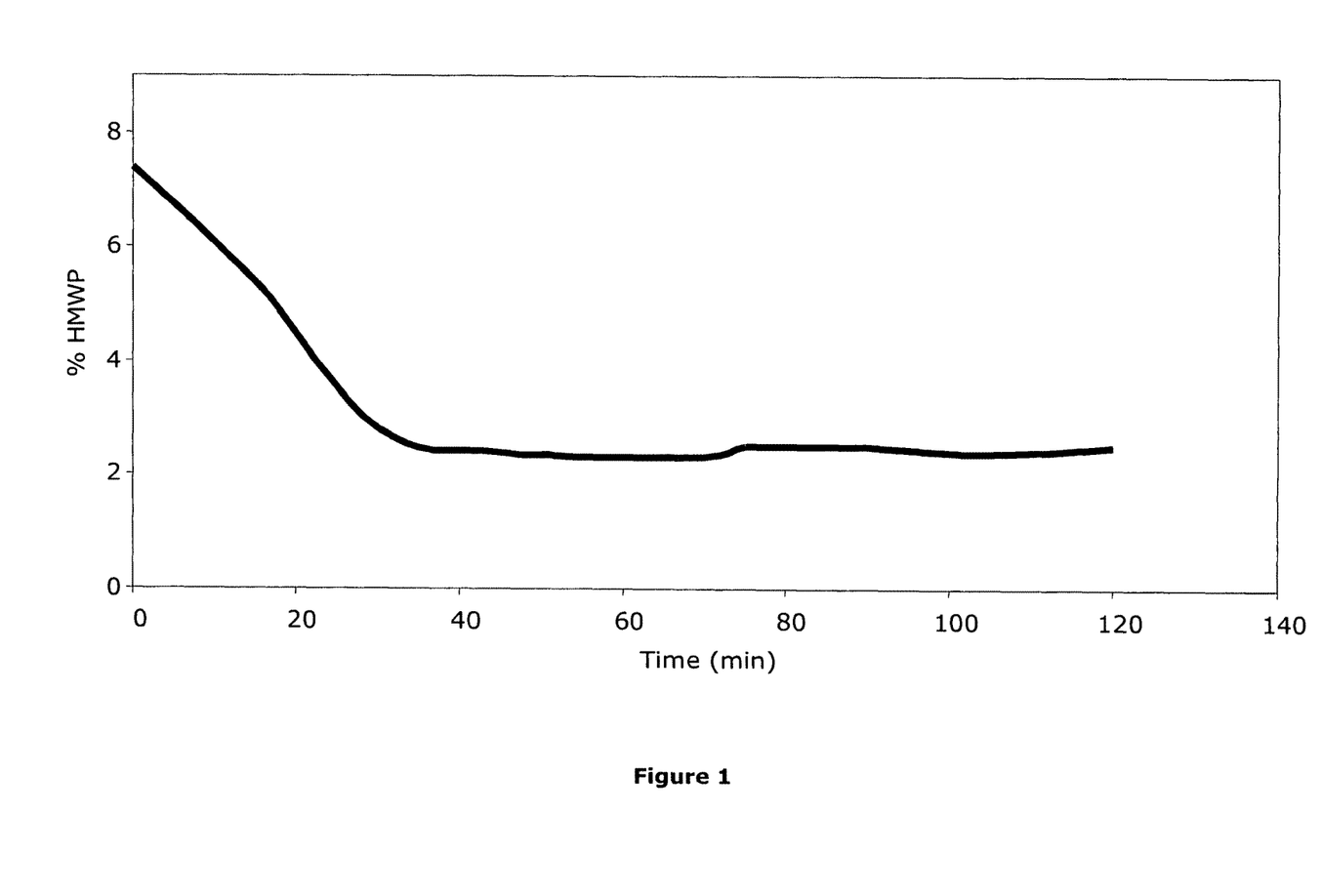
FIG. 1 illustrates the development of the dimer content in a V158D/E296V/M298Q-FVII composition sample that is heat treated at 37° C. for 120 minutes. Scale: time in minutes.

The development of the reduction of the dimer content for a similar experiment conducted for a total of 120 minutes is illustrated in FIG. 1. The experiment was monitored by frequent collection of samples; quick freezing of the samples to −80° C.; and subsequent analysis (see below).

Comparative Example 1—Storing Factor VIIa Variant at 5-8° C.

A 1.5 mg/mL solution of a FVIIa variant in 15 mM $CaCl_2$, 30 mM NaCl, 10 mM Histidine, pH 6.0 (at 5° C.) was filtered through a 0.22 micron filter into a 700 mL HDPE bottle. pH was adjusted to 5.8 (at 5° C.) using 1M HCl or 1M NaOH. The bottle was placed in a water bath with a temperature of 5-8° C. After 60 minutes, the reaction was stopped by placing the bottle in ice.

The initial dimer content was 7.7%—After the treatment it was 7.9%.

Example 2—Prolonged Heat Treatment of Factor VIIa Variant at 23° C. and 37° C.

Figure 2:
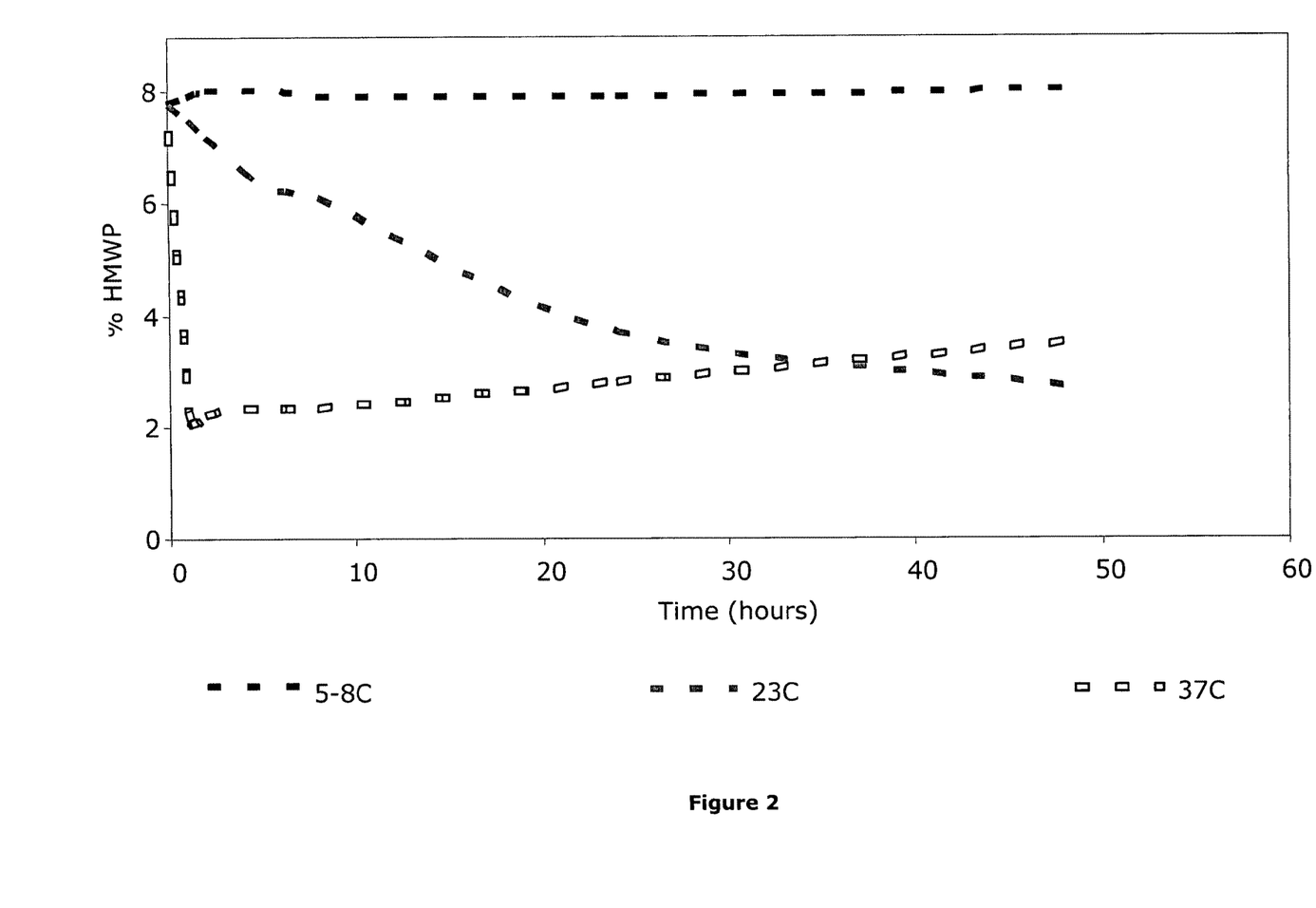
FIG. 2 illustrates the development of the dimer content in three otherwise identical V158D/E296V/M298Q-FVII composition samples that are either heated at 23° C. or 37° C., or stored at 5-8° C. (control), for 48 hours. Scale: time in hours.

A heat treatment experiment at 37° C. essentially as described in Example 1 (pH 5.7) was conducted for a total of 48 hours and a similar experiment at 23° C. was conducted for a total of 48 hours. Both experiments were monitored by frequent collection of samples; quick freezing of the samples to −80° C.; and subsequent analysis (see below). The development of the reduction of the dimer content utilizing the two different temperatures is illustrated in FIG. 2. At 37° C., a rapid drop in the dimer content was observed, whereas the decrease in dimer content for the sample at 23° C. was slower and the dimer content had possibly not reached its minimum after 48 hours. These types of experiments can be used to determine the optimal conditions (the sufficient period for the heat treatment) for other Factor VII polypeptides and at other chosen temperatures.

For comparison, a sample (similar to Comparative Example 1; pH 5.7) was left for a total of 48 hours at 5-8° C. A slight increase in dimer content was observed in this instance (see FIG. 2; upper curve).

Example 3—Prolonged Heat Treatment of Factor VIIa Variant at pH 9.5

Figure 4:
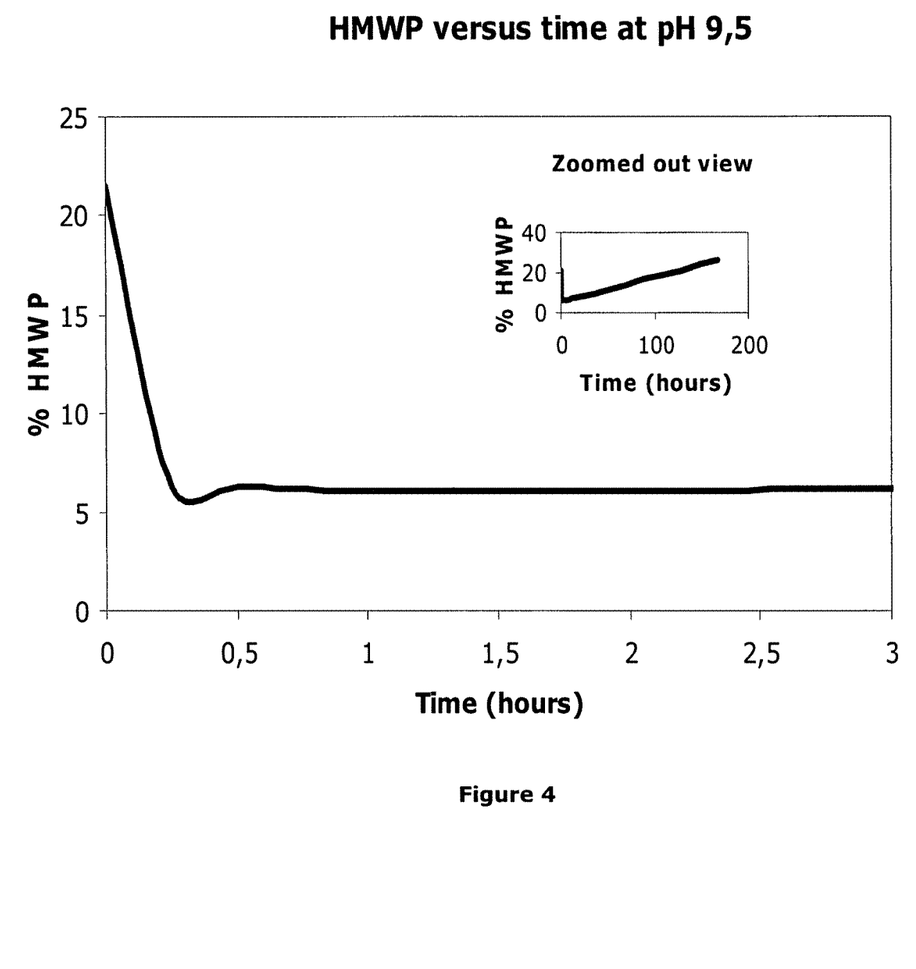
FIG. 4 illustrates the development of the dimer content in a V158D/E296V/M298Q-FVII composition sample wherein the pH was adjusted to 9.5 before heat treatment at 37° C. for 168 hours. Scale: time in hours.

A heat treatment experiment, essentially as described in Example 1, was conducted for a total of 168 hours; however, the initial pH adjustment was increased from pH 5.8 to pH 9.5. The experiment was monitored by frequent collection of samples; quick freezing of the samples to −80° C.; and subsequent analysis. The development of the reduction of the dimer content at the elevated pH is illustrated in FIG. 4. At pH 9.5 a similar rapid drop in the dimer content was observed, followed by a slow dimer formation.

The invention claimed is:

1. A method of reducing the content of dimers in a composition comprising a wild-type Factor VII, said method comprising:
    (a) heating the composition having a pH in the range of 5.0-10.0 as determined at 5° C. to a temperature in the range of 20-50° C. for a period of at least 5 minutes; and
    (b) subsequently cooling the composition to a temperature of at the most 10° C.,
    wherein the level of dimers in said composition expressed as percent-points relative to the total pool of the wild-type Factor VII has been reduced by at least a factor of 2.

2. The method of claim 1, wherein the temperature in (a) is in the range of 30-45° C. and the heating period in (a) is in the range of 10-600 minutes.

3. The method of claim 1, wherein the composition pH is in the range of 5.0-6.5 in (a).

4. The method of claim 1, wherein the composition further comprises a calcium salt.

5. The method of claim 1, wherein the wild-type Factor VII is activated in a step subsequent to the step of heating.

6. The method of claim 1, wherein an anion exchange chromatography step precedes (a).

* * * * *

UNITED STATES PATENT AND TRADEMARK OFFICE
CERTIFICATE OF CORRECTION

| | | |
|---|---|---|
| PATENT NO. | : 10,047,354 B2 | Page 1 of 1 |
| APPLICATION NO. | : 12/675004 | |
| DATED | : August 14, 2018 | |
| INVENTOR(S) | : Krarup | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 180 days.

Signed and Sealed this
Twenty-seventh Day of August, 2019

Andrei Iancu
*Director of the United States Patent and Trademark Office*